(12) United States Patent
Pullagurla et al.

(10) Patent No.: US 10,882,813 B2
(45) Date of Patent: Jan. 5, 2021

(54) METHOD FOR THE SYNTHESIS OF FERRIC ORAGANIC COMPOUNDS

(71) Applicant: Biophore India Pharmaceuticals Pvt. Ltd., Hyderabad (IN)

(72) Inventors: Manik Reddy Pullagurla, Hyderabad (IN); Mecheril Valsan Nanda Kumar, Hyderabad (IN); Jagadeesh Babu Rangisetty, Hyderabad (IN); Rajesh Bhudeti, Hyderabad (IN); Radha Nagarapu, Hyderabad (IN)

(73) Assignee: Biophore India Pharmaceuticals Pvt. Ltd., Hyderabad (IN)

( * ) Notice: Subject to any disclaimer, the term of this patent is extended or adjusted under 35 U.S.C. 154(b) by 323 days.

(21) Appl. No.: 15/536,807

(22) PCT Filed: Dec. 17, 2015

(86) PCT No.: PCT/IN2015/050208
§ 371 (c)(1),
(2) Date: Jun. 16, 2017

(87) PCT Pub. No.: WO2016/098131
PCT Pub. Date: Jun. 23, 2016

(65) Prior Publication Data
US 2019/0047934 A1 Feb. 14, 2019

(30) Foreign Application Priority Data
Dec. 17, 2014 (IN) .......................... 6352/CHE/2014

(51) Int. Cl.
*C07C 51/41* (2006.01)
*C07C 51/43* (2006.01)
*A23L 33/16* (2016.01)
*A23L 33/165* (2016.01)
*C07C 59/265* (2006.01)

(52) U.S. Cl.
CPC ............ *C07C 51/412* (2013.01); *A23L 33/16* (2016.08); *A23L 33/165* (2016.08); *C07C 51/43* (2013.01); *C07C 59/265* (2013.01)

(58) Field of Classification Search
None
See application file for complete search history.

(56) References Cited

U.S. PATENT DOCUMENTS

| 3,591,616 | A | 7/1971 | Baldt |
| 5,206,265 | A | 4/1993 | Vidic et al. |
| 6,903,235 | B2 | 6/2005 | Hsiao et al. |

(Continued)

FOREIGN PATENT DOCUMENTS

| PL | 69800 | 6/1974 |
| WO | 2004074444 A2 | 9/2004 |

OTHER PUBLICATIONS

Dirksen et al. Chemical Engineering Science vol. 46, No. 10 pp. 2389-2427, 1991.*

(Continued)

*Primary Examiner* — Clinton A Brooks
(74) *Attorney, Agent, or Firm* — The Webb Law Firm

(57) ABSTRACT

The present invention relates to an improved method for the synthesis of Ferric Citrate and also to provide an amorphous form of Ferric Citrate having an active surface area less than 14 sq.m/g.

14 Claims, 1 Drawing Sheet

(56) References Cited

U.S. PATENT DOCUMENTS

| 7,179,939 B2* | 2/2007 | Rangisetty | C07C 51/412 |
| | | | 562/587 |
| 7,767,851 B2 | 8/2010 | Kwok et al. | |
| 2014/0309298 A1 | 10/2014 | Chan et al. | |

OTHER PUBLICATIONS

IT 529984, published Jun. 30, 1955, English-language Abstract is provided and is relevant for reasons indication in specification.
JP 18/79861, cited for its disclosure and relevance as indicated in U.S. Pat. No. 5,206,265 and the specification of the present application.

\* cited by examiner

METHOD FOR THE SYNTHESIS OF FERRIC ORAGANIC COMPOUNDS

CROSS-REFERENCE TO RELATED APPLICATIONS

This application is the United States national phase of International Application No. PCT/IN2015/050208 filed Dec. 17, 2015, and claims priority to Indian Patent Application No. 6352/CHE/2014 filed Dec. 17, 2014, the disclosures of which are hereby incorporated in their entirety by reference.

FIELD OF INVENTION

The present invention describes a novel process for the preparation of pharmaceutical grade Ferric Citrate (I) used for the treatment of a various disorders such as hyperphosphatemia and metabolic acidosis. Ferric Citrate is also a common nutritional supplement against iron deficiency.

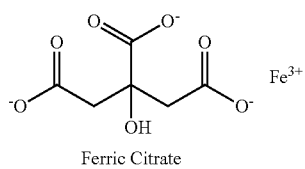

Ferric Citrate (I)

BACKGROUND OF THE INVENTION

Ferric Citrate or Iron (III) citrate is chemically known as Iron (III) 2-hydroxypropane-1,2,3-tricarboxylate. Ferric Citrate was approved by the U.S. Food and Drug Administration on Sep. 5, 2014 for the control of serum phosphorous levels in patients with treatment of chronic kidney disease (CKD) on dialysis. Ferric Citrate is garnet red or pale brown odorless powder.

The following patents and applications describe the synthesis of Ferric Citrate.

PL 69800 describes the general synthetic approach for the production of Ferric Citrate and involves the reaction of ferric hydroxide with citric acid under heating for 120 min after complete dissolution; the resulting solution was filtered to remove undissolved ferric hydroxide and evaporated at 35° and 20-30 mm Hg to a thick syrup. The obtained crude was treated with methanol to precipitate methanol.

IT529984 describes another process for the preparation of Ferric Citrate using Iron filings by heating a mixture of Iron filings and aqueous citric acid at 80° C. for 14-16 hrs followed by oxidation with nitric acid.

JP 18/79861 application discloses a process for the production of Iron complex from alkali citrate and iron carbonate followed by reaction with sodium citrate to obtain Ferric Citrate consisting of 60% of iron.

U.S. Pat. No. 5,206,265 discloses a process for the preparation of Ferric Citrate, which involves the reaction of ferric chloride hexahydrate with sodium bicarbonate followed by addition of trisodium citrate. The resulting solution was dialyzed to remove low molecular weight compounds and freeze dried.

U.S. Pat. No. 7,767,851 B2 describes a process for the synthesis of Ferric Citrate by adding an alkaline metal hydroxide solution to a ferric chloride solution and isolating a ferric hydroxide precipitate. Adding citric acid to the ferric hydroxide in water suspension followed by heating, precipitates the solid form of Ferric Citrate.

U.S. Pat. No. 6,903,235 B2 describes another method for the synthesis of Ferric Citrate by mixing solid citric acid with a solid ferric salt to form a mixture followed by addition of alcohol to the mixture and filtering the solid Ferric Citrate.

Most of the reported procedures in the prior art processes are associated with one or other drawbacks and the Ferric Citrate produced by most of the prior art processes was not suitable in the pharmaceutical applications. Moreover, some of the reported processes are very tedious and not suitable for an industrial scale production. In order to overcome the problems associated with prior art, there is a need to develop an efficient and cost effective method for the commercial scale production of pharmaceutical grade Ferric Citrate, which meets all the required specification as a drug.

SUMMARY OF THE INVENTION

In light of the forgoing deficiencies in the prior art, one of the object of the invention is to provide pharmaceutical grade Ferric Citrate.

Another object of the invention is to develop an improved process for the synthesis of pharmaceutical grade Ferric Citrate having an active surface area less than 14 sq.m/g.

Yet another object of the invention is to provide alternate method for the preparation of amorphous form of Ferric Citrate with BET less than 14 sq.m/g.

Another object of the present invention is to provide Ferric Citrate which has intrinsic dissolution rate of about 0.1-1.5 mg/cm$^2$/min.

The present invention provides an improved process for the preparation of Ferric Citrate of formula I. The below process also provides Ferric Citrate having an active surface area less than 14 sq.m/g,

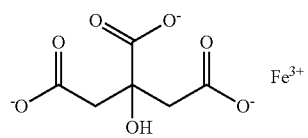

Formula I which comprises:

a) adding alkali metal carbonate to an aqueous solution of ferric chloride at 25-30° C.;

b) isolating a solid ferric hydroxide (various forms of ferric hydroxides such as hydrated ferric oxide, ferric oxyhydroxide, polymeric ferric hydroxide, ferric hydroxide gel) at pH ranging from 6.8.0 to 8.5;

c) adding ferric hydroxide to an aqueous solution of citric acid monohydrate and heating at 80 to 120° C.;

d) reducing the volume of water to 60% to 30% followed by precipitation of Ferric Citrate by adding it to water miscible organic solvent at 25-30° C. or adding water miscible organic solvent to it;

e) optional purification of Ferric Citrate from a water miscible organic solvent, alternatively from a mixture of water and water miscible organic solvent.

In another embodiment, the present invention relates to a process for the preparation of amorphous form of Ferric Citrate with defined water content, which comprises
 a) Purification of Ferric Citrate from water miscible organic solvent
 b) drying the product under vacuum at 25-30° C.

The present invention is schematically represented as follows.

Scheme 1

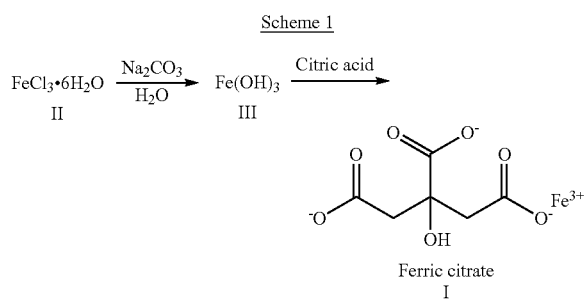

BRIEF DESCRIPTION OF THE DRAWINGS

In drawings which illustrate specific embodiments of the invention, but which should not be construed as restricting the scope of the invention in any way.

DETAILED DESCRIPTION OF THE INVENTION

Figure 1:
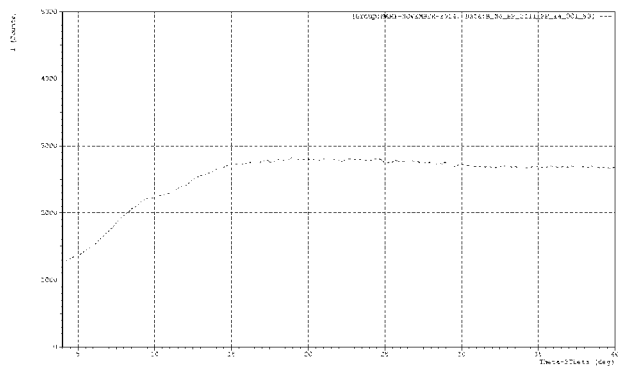
FIG. 1 is an X-ray diffraction spectrum of the Ferric Citrate.

In one embodiment, this invention provides an alternate method for the synthesis of ferric organic compounds such as Ferric Citrate having an active surface area less than 14 sq.m/g, which comprises the reaction of ferric chloride with alkali metal carbonate to form a colloidal suspension of ferric hydroxide (III), which is further treated with aqueous solution of citric acid or citric acid monohydrate to form Ferric Citrate. Finally the Ferric Citrate was precipitated from aqueous solution by reducing the volume of water and mixing water miscible organic solvent, which is optionally further purified from water miscible organic solvent, alternatively from a mixture of water and water miscible organic solvent.

In another embodiment, the preparation of colloidal suspension of ferric hydroxide of formula III involves the addition of alkali metal carbonate to an aqueous solution of ferric chloride hexahydrate with the liberation of carbon dioxide gas at 25-30° C.

Alternatively, the preparation of ferric hydroxide involves the formation of ferric carbonate by reaction of ferric chloride hexahydrate with sodium carbonate, which is further converted into ferric hydroxide by removal of excess carbon dioxide gas by purging of nitrogen gas in the reaction at a temperature ranging from 15 to 40° C.

In another aspect of the invention, the alkali metal carbonate used was selected from carbonates such as sodium carbonate, potassium carbonate, calcium carbonate or the like.

In an aspect of the invention, the process comprises the addition of 20 to 50% aqueous solution of sodium carbonate to an aqueous solution of ferric chloride hexahydrate and adjusting the pH of the solution to 6.8 to 8.5 at a temperature ranging from 15 to 40° C.

The precipitated ferric hydroxide was filtered and washed with excess water to remove the excess chloride content or to maintain less than 100 ppm or to the non-detectable level.

In the next step, the ferric hydroxide isolated was treated with citric acid, more preferably citric acid monohydrate and heated the suspension to 80 to 150° C. depending up on the reaction volume. The quantity of citric acid can vary from 0.9 to 2 equivalents and in one aspect the quantity used ranges from 1.25 to 1.5 equiv.

In one aspect, the reaction temperature ranges from 100 to 130° C. and the reaction was maintained for 3 to 24 h, more preferably the reaction was carried for 12 to 16 h.

Ferric Citrate was isolated by reducing the water volume to 60% to 30% and precipitating the product by adding water miscible organic solvent.

Finally the precipitated Ferric Citrate was purified from a water miscible organic solvent or from a mixture of water and water miscible organic solvent to obtain the pharmaceutical grade Ferric Citrate, which meets all the standard specification.

In another aspect, the water miscible organic solvent used in the present invention for the precipitation of Ferric Citrate is selected from the group of protic and aprotic solvents. The preferred protic solvents are alcohols like methanol, ethanol, and isopropyl alcohol; Aprotic solvent is selected from the group comprising carbonyl compounds like acetone, 2-butanone, methyl tertiary butyl ketone; ethers like THF, 1,4-dioxane; amides like dimethyl formamide, dimethyl acetamide; other solvents like dimethyl sulfoxide, acetonitrile.

The process further comprises the drying of the purified Ferric Citrate, more preferably the purified Ferric Citrate is dried under vacuum at a temperature less than 30° C. The moisture content of the product produced by this method contains about less than 25% (w/w) as determined by general KF method after drying.

According to one embodiment of the invention Ferric Citrate produced by the method described above is having an active surface area less than 14.0 sq.m/g According to another embodiment of the invention, Ferric Citrate produced by any known or unknown methods having an active surface area (BET) greater than 14.0 sq.m/g can be converted to Ferric Citrate with active surface area (BET) less than 14.0 sq.m/g by spraying the active with a mixture of water and water miscible organic solvent or by dissolving the active with water miscible organic solvent, wherein the water miscible organic solvent is as described herein.

According to another embodiment of the invention, Ferric Citrate produced by any known or unknown methods having an active surface area (BET) greater than 14.0 sq.m/g can be converted into Ferric Citrate with active surface are (BET) less than 14 sq.m/g by treating the active with a mixture of water and water miscible organic solvent. 'Treating the active' involves spraying the ferric citrate with a mixture of water and water miscible organic solvent or by dissolving in a mixture of water and water miscible organic solvent, wherein the water miscible organic solvent is as described herein.

Ferric Citrate prepared by any known method having (BET) surface area greater than 14 sq.m/g can be taken in a tray, to that 1 volume of 10% of water in acetone solution was added over the solid and blended the sample for uniformity. The obtained solid was dried under vacuum at 50-55° C. until MC (moisture content) complies. If the surface area of sample is still greater than 14 sq.m/g, then the same process repeated until (BET) surface area is below the 14 sq.m/g.

The analysis of BET is according to the method described as: out gassing a portion of the test sample, about 100 mg at 90° C. for 1 hour at ambient pressure using nitrogen as the adsorbate gas.

Figure 2:
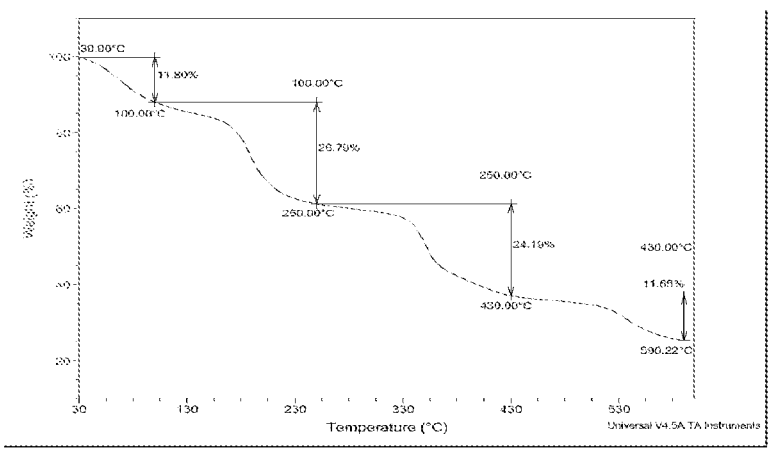
FIG. 2 is a thermo gravimetric analysis of Ferric Citrate.

In one aspect of the invention Ferric Citrate or Iron (III) citrate produced by this method is amorphous powder, which is characterized by X-Ray powder diffraction method as shown in FIG. 1 and TGA as shown in FIG. 2.

In yet another aspect of the invention the Ferric Citrate obtained from the present invention have the intrinsic dissolution rate of about 0.1-1.5 mg/cm$^2$/min In conclusion, the authors have disclosed an improved industrial scale process for the synthesis of Ferric Citrate.

The following examples further illustrate the present invention, but should not be construed in anyway as to limit its scope.

Example I

Preparation of Ferric Citrate of Formula I 100 g of Ferric chloride hexahydrate was dissolved in water, adjusted pH of the solution to 8.0-8.5 with 1200 ml of 20% Sodium carbonate solution and stirred the solution for 90 minutes at 25-30° C. Filtered the precipitated solid and slurred in water to remove excess chloride (less than 100 ppm). The obtained solid was added to a solution containing 1.5 eq. of Citric acid monohydrate dissolved in water at 25-30° C., heated the solution to 100-120° C. for 15-16 hrs and filtered through hiflo bed. The resulting filtrate was passed through micron filter and reduced the volume of solvent to 30% of its volume under vacuum at below 50° C. and precipitated final product by adding 2000 ml of acetone. The obtained Ferric Citrate was purified by suspending in 300 ml of acetone, filtered and dried under vacuum at 25-30° C. The final product obtained as an amorphous powder with BET active surface area less than 14 sq.m/g
  Yield: 55-65%
  Moisture content: 18%
  Specific surface area: 12.36 sq.m/g
  Chloride content: less than 20 ppm Example II Preparation of Ferric Citrate of Formula I 100 g of Ferric chloride hexahydrate was dissolved in water, adjusted pH of the solution to 8.0-8.5 with 1000 ml of 20% potassium carbonate solution and stirred the solution for 90 minutes at 25-30° C. Filtered the precipitated solid and slurred in water to remove excess chloride (less than 100 ppm). The obtained solid was added to a solution containing 1.5 eq. of Citric acid monohydrate dissolved in water at 25-30° C., heated the solution to 100-120° C. for 15-16 hrs and filtered through hiflo bed. The resulting filtrate was passed through micron filter and reduced the volume of solvent to 30% of its volume under vacuum at below 50° C. and precipitated final product by adding 1500 ml of Isopropyl alcohol. The obtained Ferric Citrate was purified by suspending in 300 ml of Isopropyl alcohol, filtered and dried under vacuum at 25-30° C. The final product obtained as an amorphous powder with BET active surface area less than 14 sq.m/g
  Yield: 55-65%
  Moisture content: 18.6%
  Specific surface area: 10.6 sq.m/g
  Chloride content: less than 20 ppm Example III Preparation of Ferric Citrate of Formula I 100 g of Ferric chloride hexahydrate was dissolved in water, adjusted pH of the solution to 8.0-8.5 with 1500 ml of 20% Calcium carbonate solution and stirred the solution for 90 minutes at 25-30° C. Filtered the precipitated solid and slurred in water to remove excess chloride (less than 100 ppm). The obtained solid was added to a solution containing 1.5 eq. of Citric acid monohydrate dissolved in water at 25-30° C., heated the solution to 100-120° C. for 15-16 hrs and filtered through hiflo bed. The resulting filtrate was passed through micron filter and reduced the volume of solvent to 30% of its volume under vacuum at below 50° C. and precipitated final product by adding 2500 ml of methanol. The obtained Ferric Citrate was purified by suspending in 300 ml of methanol, filtered and dried under vacuum at 25-30° C. The final product obtained as an amorphous powder and specific surface area is less than 14 sq.m/g
  Yield: 55-65%
  Moisture content: 9.3%
  Specific surface area: 12.0 sq.m/g
  Chloride content: less than 20 ppm Example IV Preparation of Ferric Citrate of Formula I 100 g of Ferric chloride hexahydrate was dissolved in water, adjusted pH of the solution to 7.0-8.0 with 1400 ml of 20% Sodium carbonate solution and stirred the solution for 90 minutes at 25-30° C. Filtered the precipitated solid and slurred in water to remove excess chloride (less than 100 ppm). The obtained solid was added to a solution containing 1.5 eq. of Citric acid monohydrate dissolved in water at 25-30° C., heated the solution to 100-120° C. for 15-16 hrs and filtered through hiflo bed. The resulting filtrate was passed through micron filter and reduced the volume of solvent to 30% of its volume under vacuum at below 50° C. and precipitated final product by adding 2000 ml of Isopropyl alcohol. The obtained Ferric Citrate was purified by suspending in 300 ml of acetone, filtered and dried under vacuum at 25-30° C. The final product obtained as an amorphous powder with BET active surface area less than 14 sq.m/g
  Yield: 55-60%
  Moisture content: 17.5%
  Specific surface area: 11.0 sq.m/g
  Intrinsic dissolution rate: 0.231 mg/sq.cm/min
  Chloride content: less than 20 ppm Example V Preparation of Ferric Citrate of Formula I 100 g of Ferric chloride hexahydrate was dissolved in water, adjusted pH of the solution to 6.8-8.0 with 400 ml of 20% Sodium carbonate solution and stirred the solution for 60-70 minutes at 10-15° C. Filtered the precipitated solid and slurred in water to remove excess chloride (less than 100 ppm). The obtained solid was added to a solution containing 1.5 eq. of Citric acid monohydrate dissolved in water at 25-30° C., heated the solution to 80-85° C. for 1-2 hrs until and filtered through hiflo bed. The resulting filtrate was passed through micron filter and reduced the volume of solvent to 30% of its volume under vacuum at below 50° C. andthe filtrate is then added to 1000 ml of acetone. The obtained Ferric Citrate solid was purified by suspending in 300 ml of acetone and stirred the reaction mass for 5-60 minutes. The final product was washed with acetone, filtered and dried under vacuum at 25-30° C. The final product obtained washed with acetone and as an amorphous powder with BET active surface area less than 14 sq.m/g Yield: 55-65%
Moisture content: 18%
Chloride content: less than 20 ppm
Specific surface area: 7.8 sq.m/g
Intrinsic dissolution rate is 0.31 mg/sq.cm/min Example VI 100 g of Ferric Citrate (surface area is 28.6. Sq.m/g) was taken in a rotocone vacuum dryer (rcvd), to this 150 ml of water and acetone mixture prepared by mixing 15 ml of water in 135 ml of acetone was added and blended the mixture for 1-2 hrs at 25-30° C. The obtained solid was dried under vacuum at 50-55° C. until MC complies (MC limit NMT 15). Surface area of the sample is 10.3 sq.m/g.

If the surface area of the sample is still greater than 14 sq.m/g, then repeat the same process until surface is less than 14 sq.m/g.

Example VII 100 g of Ferric Citrate (surface area is 30.0 Sq.m/g) was taken in a rotocone vacuum dryer (rcvd), to this 100 ml of water and acetone mixture prepared by mixing 10 ml of water in 100 ml of acetone was added and blended the mixture for 1-2 hrs at 25-30° C. The obtained solid was dried under vacuum at 50-55° C. until MC complies (MC limit NMT 15). Surface area of the sample is 20.0 sq.m/g. Repeated the same process to get the surface area 12.5 sq.m/g.

We claim:

1. A process for preparing Ferric Citrate having (BET) surface area less than 14 $m^2/g$ and with intrinsic dissolution rate of about 0.1-1.5 $mg/cm^2/min$, the process comprising:
   a) adding alkali metal carbonate to an aqueous solution of ferric chloride in the range of 25-30° C.;
   b) isolating solid ferric hydroxide at a pH in the range of 6.8 to 8.5;
   c) adding ferric hydroxide to an aqueous solution of citric acid monohydrate and heating in the range of 80 to 120° C.; and
   d) reducing the volume of water from 60% to 30% followed by precipitation of Ferric Citrate by one of adding it to water miscible organic solvent in the range of 25-30° C. and adding water miscible organic solvent to it.

2. The process as claimed in claim 1, wherein the alkali metal carbonate comprises at least one of the following: sodium carbonate, potassium carbonate, and calcium carbonate.

3. The process as claimed in claim 1, wherein the water miscible organic solvent is protic solvent or aprotic solvent.

4. The process as claimed in claim 3, wherein the protic solvent comprises at least one of the following: alcohol, methanol, ethanol, and isopropyl alcohol.

5. The process as claimed in claim 3, wherein the aprotic solvent comprises at least one of the following: a carbonyl compound selected from acetone, 2-butanone or methyl tertiary butyl ketone; an ether selected from THF or 1,4-dioxane; an amide selected from dimethyl formamide or dimethyl acetamide; or another solvent selected from dimethyl sulfoxide or acetonitrile.

6. A process for preparing Ferric Citrate having (BET) active surface area of less than 14 $m^2/g$, comprising:
   a) treating 1 volume of 10% of water in water miscible organic solvent to Ferric Citrate having (BET) surface area greater than 14 $m^2/g$; and
   b) optionally blending the sample for uniformity.

7. The process as claimed in claim 6, wherein the water miscible organic solvent is protic solvent or aprotic solvent.

8. The process as claimed in claim 7, wherein the protic solvent comprises at least one of the following: alcohols, methanol, ethanol, and isopropyl alcohol.

9. The process as claimed in claim 7, wherein the aprotic solvent comprises at least one of the following: a carbonyl compound selected from acetone, 2-butanone or methyl tertiary butyl ketone; an ether selected from THF or 1,4-dioxane; an amide selected from dimethyl formamide or dimethyl acetamide; or another solvent selected from dimethyl sulfoxide or acetonitrile.

10. A process for reducing (BET) active surface area of Ferric Citrate to less than 14 $m^2/g$, comprising:
    a) treating 1 volume of 10% of water in water miscible organic solvent to Ferric Citrate having (BET) surface area greater than 14 $m^2/g$; and
    b) optionally blending the sample for uniformity.

11. The process as claimed in claim 10, wherein the water miscible organic solvent is protic solvent or aprotic solvent.

12. The process as claimed in claim 11, wherein the protic solvent comprises at least one of the following: alcohols, methanol, ethanol, and isopropyl alcohol.

13. The process as claimed in claim 11, wherein the aprotic solvent comprises at least one of the following: a carbonyl compound selected from acetone, 2-butanone or methyl tertiary butyl ketone; an ether selected from THF or 1,4-dioxane; an amide selected from dimethyl formamide or dimethyl acetamide; or another solvent selected from dimethyl sulfoxide or acetonitrile.

14. The process as claimed in claim 1, wherein,
    the alkali metal carbonate comprises sodium carbonate,
    the water miscible organic solvent is acetone, and
    the ferric hydroxide is added to an aqueous solution of citric acid monohydrate and heated in the range of 80 to 85° C. for 1-2 hours.

* * * * *